United States Patent [19]
Durrant et al.

[11] Patent Number: 4,699,924
[45] Date of Patent: Oct. 13, 1987

[54] SKIN TREATMENT COMPOSITION

[75] Inventors: James A. Durrant, Merseyside; Michael R. Lowry, Chester, both of England

[73] Assignee: Lever Brothers Company, New York, N.Y.

[21] Appl. No.: 572,796

[22] Filed: Jan. 23, 1984

[30] Foreign Application Priority Data

Feb. 1, 1983 [GB] United Kingdom ............... 8302683

[51] Int. Cl.$^4$ .............................................. A61K 31/20
[52] U.S. Cl. ..................................... 514/558; 514/738
[58] Field of Search ................ 424/317, 318; 514/558, 514/738

[56] References Cited

U.S. PATENT DOCUMENTS

| | | | |
|---|---|---|---|
| 3,988,470 | 10/1976 | Van Scott et al. | 424/317 |
| 4,105,782 | 8/1978 | Yu et al. | 424/283 |
| 4,197,316 | 4/1980 | Yu et al. | 424/317 |
| 4,424,234 | 1/1984 | Alderson et al. | 424/317 |
| 4,507,319 | 3/1985 | Barratt et al. | 514/546 |

FOREIGN PATENT DOCUMENTS

| | | |
|---|---|---|
| 43738 | 7/1981 | European Pat. Off. . |
| 2817133 | 11/1978 | Fed. Rep. of Germany . |
| 884688 | 3/1960 | United Kingdom . |

OTHER PUBLICATIONS

"A Formulary of Cosmetic Preparations", M. & E. Ash (1977) pp. 259, 291 and 308.

Primary Examiner—Leonard Schenkman
Attorney, Agent, or Firm—Milton L. Honig; James J. Farrell

[57] ABSTRACT

A cosmetically acceptable product for topical application to human skin comprises a selected amphiphilic compound having a log partition coefficient in octanol/water of from 0.5 to 3.5; emulsifier which is normally solid at 20° C., which has an average HLB value of from 5 to 11, and which is capable with water of forming a gel phase having an X-ray reflection of from 0.37 to 0.44 nm and which permits substantially no co-crystallisation therewith of the amphiphilic compound; an activity enhancer which is capable, at a concentration of 5% by weight of increasing the cloud point temperature of a 0.025M aqueous solution of polyoxyethylene (8) nonylphenyl ether by at least 10° C.; and water, the product having an aqueous phase and a gel phase.

Optionally the product can also comprise an "oil" having a dielectric constant not greater than 3.0, in which case the product will also comprise an oily phase.

7 Claims, No Drawings

SKIN TREATMENT COMPOSITION

The invention relates to cosmetically acceptable products, particularly oil-in-water emulsions containing an amphiphilic compound which possesses a skin benefit property.

An amphiphilic compound is one which possesses in the same molecule distinct regions of lipophilic and hydrophilic character. When incorporated in an emulsion, an amphiphilic compound will accordingly normally partition into both the aqueous and the oily phases.

If such an emulsion is then applied to human skin, delivery of the amphiphlic compound selectively to the skin surface can be impaired due to the fact that a significant amount remains in the oily phase.

It has now been discovered that a totally new type of product can be formed between water, a special normally solid emulsifier capable of forming a gel phase, and an activity enhancer, which together provides a vehicle for the amphiphilic compound with enhanced delivery properties due to its partition almost exclusively into the aqueous phase.

It is accordingly with the provision of a superior product containing an amphiphilic compound having skin benefit properties, which possesses the ability to deliver to human skin an unexpectedly high proportion of the amphiphilic compound, that this invention is concerned.

Accordingly, the invention provides a cosmetically acceptable product for topical application to human skin which comprises:

(i) from 0.001 to 20% by weight of an amphiphilic compound having a log partition coefficient in octanol/water of from 0.5 to 3.5, provided that when the amphiphilic compound is one having an unbranched alkyl chain, that chain contains no more than 12 carbon atoms;

(ii) from 1 to 20% by weight of emulsifier which is normally solid at 20° C., which has an average HLB value of from 5 to 11, and which is capable with water of forming a gel phase having an X-ray reflection of from 0.37 to 0.44 nm and which permits substantially no co-crystallisation therewith of the amphiphilic compound;

(iii) from 0.1 to 50% by weight of an activity enhancer which is capable, at a concentration of 5% by weight of increasing the cloud point temperature of a 0.025M aqueous solution of polyoxyethylene (8) nonylphenyl ether by at least 10° C.; and (iv) from 5 to 98.899% by weight of water;

the product having an aqueous phase which forms from 5 to 99% by volume and a gel phase which forms from 1 to 95% by volume.

The product of the invention is accordingly one in which the aqueous phase forms from 5 to 99%, preferably from 50 to 90% by volume and the gel phase forms from 1 to 95%, preferably from 5 to 50% by volume. The gel phase comprises long straight hydrophobic alkyl chains ($C_{14}$ to $C_{20}$) with an average HLB value of no more than 11, the alkyl chain groups being rigid and packed in a hexagonal lattice; they undergo rapid rotation about the chain axis and are characterised by having an X-ray reflection of from 0.37 to 0.44 nm. It should be explained that similar systems having an X-ray reflection of less than 0.37 nm are solids and those having an X-ray reflection of greater than 0.44 nm form a lamellar phase which does not possess the properties and advantages of a gel phase as described herein.

The formation, structure and properties of the gel phase are further described in "Biological Membranes: Physical Fact & Function" Ed. by Denis Chapman (1968).

It has been discovered that incorporation of an amphiphilic compound into a product in which such a gel phase is already preformed results in partition of a substantial proportion of the amphiphilic compound into the aqueous phase, with the result that the amphiphilic compound possesses greater affinity for human skin following topical application of the product, than would be the case if the amphiphilic compound had been incorporated into a normal oil-in-water emulsion. This is because the gel phase resists partition into it and co-crystallisation with it of the amphiphilic compound, so that the availability of the amphiphilic compound to the skin from the aqueous phase, following topical application of the product, is thereby enhanced.

Amphiphilic compound

The product comprises an amphiphilic compound which is characterised by its ability to partition between octanol and water and is accordingly defined as having a log partition coefficient in octanol/water of from 0.5 to 3.5.

The amphiphilic compound is further characterised by the proviso that when an unbranched alkyl chain is present in the molecule, then that chain contains no more than 12 carbon atoms.

It should be explained that if the amphiphilic compound is one having an unbranched alkyl chain with more than 12 carbon atoms, then it can co-crystallise in the gel phase, whereas it will not behave in this way if the unbranched alkyl chain contains no more than 12 carbon atoms.

Examples of amphiphilic compounds which fulfil the above criteria and which are suitable for use in the products of the invention are given below together with their respective log partition coefficients. It is to be understood that this selection of preferred amphiphilic compounds is given by way of example and that it does not accordingly constitute an exhaustive list to which the invention is limited.

|  | Log partition coefficient of from 0.50 to 1.00 (octanol/water at 20° C.) |
|---|---|
| morphine | 0.76 |
| triethyl citrate | 0.67 |
| sulphamonomethoxine | 0.85 |
| adenosine diphosphate | 0.89 |
| ephedrine | 0.93 |
| sulphamethoxazole | 0.88 |
| 5-ethyl-5-i-propyl barbituric acid | 0.97 |
| 5,5-diethyl barbituric acid | 0.65 |
| p-methylbenzene sulphonamide | 0.82 |
| o-methylbenzene sulphonamide | 0.84 |
| m-methylbenzene sulphonamide | 0.85 |
| p-aminobenzoic acid | 0.68 |
| saccharin | 0.91 |
| p-dihyroxybenzene | 0.59 |
| o-dihydroxybenzene | 0.80 |
| p-nitrobenzene sulphonamide | 0.64 |
| m-nitrobezene sulphonamide | 0.55 |
| 2-ethyl-2-propanol | 0.89 |
| crotonic acid | 0.72 |

| | Log partition coefficient of from 1.01 to 1.50 (octanol/water at 20° C.) |
|---|---|
| erythromycin | 1.26 |
| 4'-hydroxyerythromycin | 1.44 |
| colchicine | 1.03 |
| codeine | 1.01 |
| α-hydroxy benzyl penicillin | 1.40 |
| cyclobarbital | 1.20 |
| 5-ethyl-5-phenyl barbituric acid | 1.42 |
| chloramphenicol | 1.14 |
| nicotine | 1.17 |
| niacinamide | 1.37 |
| 4-methyl-6-(2,4,6-trimethyl-pentyl)-2-(1H)—pyridone | 1.28 |
| 5,5-dimethyl, 1-methyl barbituric acid | 1.09 |
| acetyl salicyclic acid | 1.23 |
| coumarin | 1.39 |
| 2-phenyl ethanol | 1.36 |
| ethyl nicotinate | 1.32 |
| m-hydroxybenzoic | 1.50 |
| benzimidazole | 1.34 |
| phenol | 1.46 |

| | Log partition coefficient of from 1.51 to 2.00 (octanol/water at 20° C.) |
|---|---|
| hydrocortisone | 1.53 |
| strychnine | 1.93 |
| quinine | 1.73 |
| thebaine | 1.91 |
| atropine | 1.79 |
| benzyl pencillin | 1.83 |
| sulphaphenzole | 1.57 |
| procaine | 1.87 |
| sulphadimethoxine | 1.56 |
| adenosine triphosphate | 1.64 |
| azelaic acid | 1.57 |
| amphetamine | 1.63 |
| N—acetyl O—aminobenzoic acid | 1.88 |
| O—hydroxybenzaldehyde | 1.70 |
| benzoic acid | 1.87 |

| | Log partition coefficient of from 2.01 to 3.50 (octanol/water at 20° C.) |
|---|---|
| salicylic acid | 2.26 |
| 2-hydroxyoctanoic acid | 2.24 |
| 2-ketooctanoic acid | 3.20 |

The amphiphilic compound to be incorporated in the product of the invention should form from 0.001 to 20%, preferably from 0.01 to 10% and most preferably from 0.01 to 5% by weight of the product.

The appropriate amount of amphiphilic compound employed will depend on its function and property on the skin and the purpose for which it is applied.

Emulsifier

The product according to the invention will also comprise one or more emulsifiers which are normally solid at room temperature, that is at 20° C., and which have an average HLB value of from 5 to 11 and which are capable of producing a gel phase with water.

Examples of preferred emulsifiers together with their respective HLB values are given below:

| Emulsifier | HLB value |
|---|---|
| BRIJ 52 (polyoxyethylene(2)cetyl ether) | 5.3 |
| ALDO MSD (glyceryl monostearate) | 5.5 |
| ARLACEL 40 (sorbitan monopalmitate) | 6.7 |
| TEGESTER PEG (polyethyleneglycol 200 monostearate) | 8.5 |
| EMEREST 2642 (polyethyleneglycol 400 distearate) | 8.5 |
| ETHOPHATE 60/15 (polyoxyethylene(5)-monostearate) | 9.0 |
| TWEEN 61 (polyoxyethylene(4)sorbitan monostearate) | 9.6 |
| HODAG 62-S (polyethylene glycol 400 distearate) | 10.5 |
| ARLACEL 165 (glyceryl monostearate) | 11.0 |

Where a mixture of more than one emulsifier is employed, it is possible that each may have an HLB value outside the range of from 5 to 11, provided that the mixture has an average HLB value within this range.

Examples of preferred mixtures of emulsifiers together with their respective average HLB values are given below:

| Emulsifier | % W/W in mixture | HLB Value individual | HLB Value mixture |
|---|---|---|---|
| BRIJ 52 (polyoxyethylene(2) cetyl ether) | 70 | 5.3 | 8.4 |
| BRIJ 58 (polyoxyethylene(20) cetyl ether) | 30 | 15.7 | |
| ALDO MSD (glycerol monostearate) | 80 | 5.5 | 7.5 |
| BRIJ 58 | 20 | 15.7 | |
| BRIJ 72 (polyoxyethylene (2)stearyl ether) | 14 | 4.9 | 10.1 |
| ARLACEL 165 (glycerol monostearate) | 86 | 11.0 | |
| BRIJ 52 | 67 | 5.3 | 7.8 |
| BRIJ 56 (polyoxyethylene (10)cetyl ether) | 33 | 12.9 | |

EMULSENE 1219 (supplied by Bush Boake Allen), a mixture of emulsifiers having an average HLB value between 5 and 11.

The emulsifier, whether a single emulsifier or mixtures thereof, to be incorporated into the product of the invention should form from 1 to 20%, preferably from 2 to 10% by weight of the emulsion.

Activity Enhancer

The product according to the invention will also comprise an activity enhancer whose presence further improves the delivery to the skin of the amphiphilic compound. The activity enhancer accordingly effectively increases the partition of the amphiphilic compound into the skin from the product when applied topically. The activity enhancer will have little or no effect on improving skin benefit such as increasing skin plasticisation when used alone: it is only when combined with the amphiphilic compound that a substantial increase in skin benefit is realised.

While screening a series of non-electrolytes for their ability to function as activity enhancers, it was observed that they were all compounds which were capable of substantially increasing the cloud point temperature of nonionic surfactants. Such compounds included short chain alkanols, diols and short chain fatty acids. By contrast, other non-electrolytes which reduce the cloud point temperature of nonionic surfactants, such as long chain alcohols, for example, butan-1-ol and cyclohexanol; polyols, for example sorbitol and propan-1,2,3-triol, do not function as activity enhancers.

An activity enhancer is accordingly defined as a non-electrolyte which is capable, at a concentration of 5% by weight of increasing the cloud point temperature of a 0.025M aqueous solution of polyoxyethylene(8)nonylphenyl ether by at least 10° C. Preferably the activity enhancer is one which is capable of increasing the cloud point temperature by at least 15° C., most preferably by at least 20° C.

It should be explained that the "cloud point" is a measure of the inverse solubility of a nonionic surfactant with temperature and can be determined by heating a standard clear aqueous solution of the nonionic surfactant until the solution becomes visibly cloudy and then measuring the temperature.

The cloud point temperature can conveniently be determined automatically using the equipment and method described by Baum et al in Mat. Res. Std. 4 26 (1964).

Examples of suitable compounds functioning as activity enhancers, together with the respective elevated cloud point temperature obtained in each case when using the standard test defined hereinbefore are listed below in Table 1.

TABLE 1

Elevation of the cloud point temperature of a 0.025 M aqueous solution of polyoxyethylene(8)nonylphenyl ether in the presence of activity enhancers

| Activity Enhancer (5% by weight) | 0.025 M aqueous solution of polyoxyethylene(8)nonyl phenyl ether (SYNPERONIC NP8 ex ICI) | |
|---|---|---|
| | Cloud point temperature (°C.) | Elevation of cloud point temperature |
| None (control) | 33.5 | 0 |
| 2-methyl propan-2-ol | 55.0 | 21.5 |
| Propan-2-ol | 56.0 | 22.5 |
| Ethyl-2hydroxypropanoate | 52.1 | 18.6 |
| Hexan-2,5-diol | 52.0 | 18.5 |
| POE(2) ethyl ether | 46.0 | 12.5 |
| Di(2-hydroxypropyl) ether | 44.8 | 11.3 |
| Pentan-2,4-diol | 48.0 | 14.5 |
| Acetone | 46.3 | 12.8 |
| POE(2) methyl ether | 43.5 | 10.0 |
| 2-hydroxypropionic acid | 45.0 | 11.5 |
| Propan-1-ol | 53.0 | 19.5 |
| 1,4 Dioxane | 44.0 | 10.5 |
| Tetrahydrofuran | 45.0 | 11.5 |
| Butan-1,4-diol | 45.0 | 11.5 |

By way of comparison, we list below in Table 2 examples of non-electrolytes which do not satisfy the cloud point test in that the increase in cloud point temperature is less than 10° C.; in some cases a reduction of cloud point temperature is observed.

TABLE 2

Elevation (or reduction) of the cloud point temperature of a 0.025 M aqueous solution of polyoxyethylene(8)nonylphenyl ether in the presence of compounds which are not "activity enhancers" as herein defined

| Compound which is not an activity enhancer (5% by weight) | 0.025 M aqueous solution of polyoxyethylene(8)nonylphenyl phenyl ether (SYNPERONIC NP8) | |
|---|---|---|
| | Cloud point temperature (°C.) | Elevation of cloud point temperature (°C.) |
| None (control) | 33.5 | 0 |
| 2-methyl propan-1-ol | 41.0 | 7.5 |
| Butan-1-ol | 36.3 | 2.8 |
| Cyclohexanol | 11.0 | −22.5 |
| Ethan-1,2-diol | 33.0 | −0.5 |
| Propan-1,2-diol | 39.0 | 5.5 |
| Butan-1,3-diol | 41.5 | 8.0 |
| Propan-1,2,3-triol | 32.2 | −1.3 |
| Morpholine | 40.0 | 6.5 |
| Dimethyl sulphoxide | 33.9 | 0.4 |

The activity enhancer should form from 0.1 to 50%, preferably from 0.5 to 25% by weight of the product.

Water

The product according to the invention will also comprise from 5 to 98.899%, preferably from 9 to 95% by weight of water which will form a substantial proportion of the aqueous phase in the emulsion.

"Oil"

The product can also optionally comprise an oil, fat or wax, herein referred to as "oil" having a dielectric constant of not greater than 3.0. It is apparent that if an "oil" possessing a higher dielectric constant is employed, then the affinity of the amphiphilic compound for the oil will be unacceptably high, and the delivery to the skin of the amphiphilic compound will thereby be impaired.

Examples of preferred "oils", when employed, together with their dielectric constants measured when they are in a liquid state are given below:

| "Oils" | Dielectric constant* |
|---|---|
| n-decane | 1.99 |
| n-dodecane | 2.02 |
| linoleic acid | 2.71 |
| oleic acid | 2.46 |
| beeswax | 2.90 |
| carnauba wax | 2.75 |
| paraffin wax | 2.05 |
| OZOKERITE WAX | 2.03 |

*as recorded in "Handbook of Chemistry & Physics" pages E 55–60, 57th Edition 1976-77

Further examples of "oils" having a dielectric constant <3.0 include mineral oil, n-tetradecane, n-hexadecane, n-octadecane, SIRIUS M85 (Paraffin Oil ex Dalton Industries), ISOPAR L ($C_{10}$–$C_{12}$ isoparaffin ex Esso), SILKOLENE 910 (paraffin jelly ex Dalton Industries).

When an oil is to be incorporated in the product of the invention, it should form up to 75%, preferably from 1 to 75%, most preferably from 1 to 30% by weight of the product.

The product can optionally also contain other hydrophilic or lipophilic materials as are conventionally employed in products which are particularly adapted to be applied topically to human skin. Examples of such optional materials include perfumes, colourants, preservatives, germicides, sunscreens and humectants.

The product can take the form of a solid or semi-solid cream or a gelled, thickened or free flowing liquid.

The product will normally be packaged in a convenient dispenser such as a bottle, jar or tube having a closure.

The invention also provides a process for the preparation of a cosmetically acceptable product for topical application to human skin which comprises the steps of:

(i) preparing an aqueous phase by mixing with water, water-soluble ingredients, other than the amphiphilic compounds, such as activity enhancers, preservatives and humectants, and heating the mixture to a temperature of at least 50° C., preferably at least 70° C.;

(ii) adding to the aqueous phase, melted emulsifier which is normally solid at 20° C., which has an average HLB value of from 5 to 11 and which is capable of forming a gel phase, with continued heating at at least 50° C., preferably at at least 75° C. and shear mixing to provide an emulsion;

(iii) cooling the emulsion to form a gel phase having an X-ray reflection of from 0.37 to 0.44 nm;

(iv) adding with continued stirring the amphiphilic compound; and (v) subsequently packaging the product so formed in a sealed container;

the product having an aqueous phase which forms from 5 to 99% by volume and a gel phase which forms from 1 to 95% by volume of the product, the amphiphilic compound forming from 0.001 to 20% by weight, the emulsifier forming from 1 to 20% by weight, the activity enhancer forming from 0.1 to 50% by weight and water forming from 5 to 98.899% by weight.

The invention further provides a process for the preparation of a cosmetically acceptable product containing "oil" suitable for topical application to human skin, which process comprises the steps of:

(i) forming an emulsion between an aqueous phase and an oily phase, comprising:
 (a) an aqueous phase containing water soluble ingredients, other than amphiphilic compounds, such as activity enhancers, preservatives and humectants;
 (b) an "oil" having a dielectric constant of not greater than 3.0; and
 (c) emulsifier normally solid at 20° C., which has an average HLB value of from 5 to 11, and which is capable of forming a gel phase with water;
at a temperature of at least 50° C., preferably at least 70° C.;

(ii) cooling the emulsion to produce a gel phase having an X-ray reflection of from 0.37 to 0.44 nm, and to solidify the "oils" with melting points above 20° C.;

(iii) adding with stirring the amphiphilic compound; and (iv) subsequently packaging the emulsion so produced in a sealed container.

the product having an aqueous phase which forms from 5 to 99% by volume, an "oil" phase which forms from 2 to 95% by volume and a gel phase which forms from 1 to 95% by volume, the amphiphilic compound forming from 0.001 to 20% by weight, the emulsifier forming from 1 to 20% by weight, the activity enhancer forming from 0.1 to 50% by weight, the "oil" forming from 1 to 75% by weight and the water forming from 5 to 97.899% by weight.

The product according to the invention is suitable for topical application to human skin and is intended to provide enhanced delivery to the skin of amphiphilic skin benefit compounds for cosmetic purposes, or of amphiphilic pharmaceutical or other healing agents for the treatment of skin disease.

A particularly preferred product is one containing, as the amphiphilic compound, 2-hydroxy octanoic acid which is capable of softening the skin by increasing the extensibility of stratum corneum and which is suited to the treatment of acne.

Evidence of delivery to skin from gel phase system of amphiphilic compound

An experiment was conducted to compare the delivery to skin of phenol, as an example of an amphiphilic compound, from an ordinary emulsion and from two products having a gel phase. These products were not strictly in accordance with the invention as no activity enhancer was present, but the experiment was designed to demonstrate the efficacy of a gel phase containing system in delivering phenol to skin.

Preparation of products

1. Control emulsion

An ordinary oil-in-water emulsion which does not contain a gel phase was prepared as follows:

Octanol (oil: dielectric contstant 10.3), 25 parts, was mixed with SYNPERONIC NP8 (liquid emulsifier HLB value 12.3), 5 parts, and phenol (amphiphilic compound), 1 part, to form an oily phase. This was heated to 70° C. and added to water, 69 parts, also heated to 70° C. with mixing to form an emulsion. This was then cooled to 20° C.

2. Test Product A

A product having a gel phase and containing a solid wax was prepared as follows:

Paraffin wax ("oil"), 25 parts, and a mixture of two normally solid emulsifiers, namely BRIJ 58, 3 parts, and ALFOL 16, 2 parts, were heated together at 70° C. to form a melt which was then added with stirring to water, 69 parts, also heated to 70° C. The emulsion so obtained was cooled to 40° C. to solidify both the paraffin wax and the emulsifiers and phenol, 1 part, was added with stirring and further cooling to 20° C.

3. Test Emulsion B

An emulsion having a gel phase and containing normally liquid oil having a dielectric constant of not more than 3.0 was prepared in the manner described for Test Product A, except that SIRIUS M85, 25 parts, the normally liquid oil was employed instead of paraffin wax.

The phenol used in the preparation of each emulsion was $C^{14}$ labelled phenol.

Application to skin and measurement of phenol

Pieces of guinea pig stratum corneum were immersed in each of the above emulsions for 20 hours, after which they were removed, blotted dry and the amount of phenol retained by the corneum was measured by a radio tracer technique using a standard methodology. The results of these measurements were as follows:

| Product | Phenol delivered to stratum corneum (moles phenol/g) |
| --- | --- |
| Control | $6.38 \times 10^{-5}$ |
| Test A | $20.46 \times 10^{-5}$ |
| Test B | $12.69 \times 10^{-5}$ |

Conclusion

It can be concluded from these results that delivery to skin of phenol, as an example of an amphiphilic compound, from a product is enhanced when a gel phase is present in the product. When the emulsion contains a normally liquid oil such as SIRIUS M85 (Test Emulsion B) then the amount of phenol delivered to the skin is doubled, whereas when a solid wax such as paraffin wax is present (Test Product A), then the amount of phenol delivered to the skin is about three times that delivered from an oridinary emulsion (Control).

Evidence of the benefit of an activity enhancer in the delivery to the skin of an amphiphilic compound An experiment was conducted to compare the delivery to skin of 2-hydroxyoctanoic acid, as an example of an amphiphilic compound, from an aqueous solution with and without activity enhancers. These solutions are not products according to the invention, since no "oil" or normally solid emulsifier was present, but the experiment nevertheless was designed to demonstrate the efficacy of activity enhancers having the requisite cloud point elevation temperature in delivering 2-hydroxyoctanoic acid to the skin.

Preparation of control and test solutions

The control and each of the test solutions comprised a 0.2M aqueous solution of 2-hydroxyoctanoic acid. The control solution contained no additives, while the test solutions each contained 5% by weight of a further additive, some which were activity enhancers as herein defined, in that they possessed the ability to elevate the cloud point of a 0.025M aqueous solution of polyoxyethylene(8)nonylphenyl ether by at least 10° C. under the conditions defined herein, while other additives possessed cloud point elevation temperatures of less than 10° C.

Increase in extensibility of stratum corneum

The ability of an additive to enhance the delivery to skin of 2-hydroxyoctanoic acid was measured in terms of the increase in extensibility of guinea pig foot pad stratum corneum following contact with each solution.

In this experiment, pieces of guinea pig foot pad stratum corneum, equilibrated at a relative humidity of 65%, were immersed in each solution for 3 hours at 20° C., and then removed, blotted dry and re-equilibrated at the same relative humidity. The extensibility of each piece of guinea pig foot pad stratum corneum was measured before and after this treatment in an extensiometer according to the method described in European Pat. No. 7785.

Results

The results of this experiment are tabulated below:

| Test Number | 0.2 M 2-hydroxyoctanoic + + additive at 5% w/w | Elevation of cloud point temperature | Increase stratum corneum extensibility |
|---|---|---|---|
| Control | No additive | — | 5 |
| 1 | propan-1,2,3-triol | −1.3 | 5 |
| 2 | ethan-1,2-diol | −0.5 | 5 |
| 3 | dimethyl sulphoxide | −0.5 | 5 |
| 4 | butan-1-ol | 2.8 | 13.2 |
| 5 | propan-1,2-diol | 5.5 | 12.6 |
| 6 | di(hydroxy propyl)ether | 11.3 | 21.6 |
| 7 | 2-hydroxy propionic acid | 11.5 | 17.1 |
| 8 | pentan-2,4-diol | 14.5 | 17.0 |
| 9 | 2-pyrrolidone | 15.5 | 28.0 |
| 10 | hexan-2,5-diol | 18.5 | 37.0 |

Conclusion

It can be concluded from these results that delivery to skin of 2-hydroxyoctanoic acid, as an example of an amphiphilic compound from an aqueous solution is greatly enhanced when the solution also contains an activity enhancer as herein defined is employed.

It can be seen by inspection of the results tabulated above that each of test solutions 1 to 5, which contain additives at 5% w/w possessing a cloud point elevation temperature of less than 10 result in an increase in stratum corneum extensibility which is less than that recorded with test solutions 6 to 10, which contain activity enhancers as herein defined. This supports the fact that the presence of an activity enhancer substantially increases the delivery to skin of the amphiphilic compound, bearing in mind that none of the additives when employed alone increases the extensibility of stratum corneum to any significant extent.

The invention is illustrated by the following Examples:

EXAMPLES 1 TO 3

The following formulations represent oil-in-water creams according to the invention that can be used in the treatment of acne.

| | % w/w | | |
|---|---|---|---|
| | 1 | 2 | 3 |
| "Oils" | | | |
| mineral oil | 4 | 2 | — |
| paraffin wax (Mp 55° C.) | — | 2 | 4 |
| Solid emulsifiers | | | |
| polyoxyethylene(10) cetyl ether* | 4 | 4 | 4 |
| cetyl alcohol* | 4 | 4 | 4 |
| Amphiphilic compounds | | | |
| 2-hydroxyoctanoic acid | 2.4 | — | 2.4 |
| 2-ketooctanoic acid | — | 2.4 | — |
| Activity enhancer | | | |
| acetone | 3 | — | — |
| butan-1,4-diol | — | 3 | — |
| hexan-2,5-diol | — | — | 3 |
| Other ingredients | | | |
| triethanolamine | ~0.75 | ~0.75 | ~0.75 |
| xantham gum | 0.3 | 0.3 | 0.3 |
| perfume | qs | qs | qs |
| preservative | 0.4 | 0.4 | 0.4 |
| water | to 100 | 100 | 100 | pH adjusted with triethanolamine to pH 4 in each case.
*a mixture of emulsifiers having an average HLB value of about 7.

Preparation of creams

The oil-in-water creams according to Examples 1, 2 and 3 were each prepared as follows:
(i) The mineral oil and/or the paraffin wax were heated to a temperature of 75° C. and the normally solid emulsifiers, polyoxyethylene(10)cetyl ether and cetyl alcohol were each added with continued heating at 75° C. to provide a melt (oily phase).

(ii) The activity enhancer, triethanolamine, xantham gum and preservative were each added to the requisite amount of water with stirring and heating to 75° C. (aqueous phase).
(iii) The oily phase was then added gradually to the aqueous phase with sheer stirring while maintaining the temperature at 75° C.
(iv) The emulsion so obtained was then cooled to 45° C. in order to solidify at least the normally solid emulsifiers and the wax present in Example formulations 2 and 3. A gel phase was obtained together with an aqueous and oily phase, the latter being solid in the case of Example formulation.
(v) The amphiphilic compounds (2-hydroxy octanoic acid or 2-ketooctanoic acid) was then mixed into the cooled emulsion to form a white viscous cream, and the cream was finally packaged in screw topped jars.

Effect of creams on pH value of human skin

The creams of Examples 1 and 3 with activity enhancers, and control creams based on the Example 1 and Example 3 formulations omitting activity enhancers and the 2-hydroxy octanoic acid, were each applied to the foreheads of a panel of 10 volunteer subjects, according to a statistically designed experiment. The area of forehead skin treated in each subject was 32 cm$^2$ and the quantity of cream applied to this area was 0.0865 g. In each case, the skin surface pH was measured at frequent intervals over four hours following application of the creams, and the cream pH value calculated in each case.
The following results were obtained:

| Cream formulation | Mean skin pH after 4 hours |
|---|---|
| Example 1 | 4.95 |
| Example 3 | 4.60 |
| Control 1 | 5.39 |
| Control 3 | |

From these results, it can be concluded that:
(i) 2-hydroxyoctanoic acid is being delivered effectively from both Example 1 and Example 3 creams, as evidenced by the lower mean pH value due to the effect of this acid.
(ii) A greater quantity of 2-hydroxyoctanoic acid is delivered to the skin from the Example 3 cream than from the Example 1 cream, thus indicating that a greater proportion of the acid is partitioned into the aqueous phase where solid paraffin wax comprises the oily phase than where liquid mineral oil comprises the oily phase.

These conclusions provide further support for preference for a solid wax over a liquid oil (even though both have a dielectric constant of not greater than 3) as shown in the foregoing experiments reported earlier in this specification.

EXAMPLES 4 TO 6

The following formulations represent an oil-in-water emulsion according to the invention which can be employed topically in the treatment of acne.

| | % w/w | | |
|---|---|---|---|
| | 4 | 5 | 6 |
| "Oils" | 5 | 5 | 5 |
| mineral oil | | | |
| Solid emulsifier EMULSENE 1219* | 7 | 7 | 7 |
| Amphiphilic compound 2-hydroxyoctanoic acid | 2 | 2.5 | 3 |
| Activity enhancer | | | |
| 2-hydroxypropionic acid | 5 | — | 5 |
| ethyl 2-hydroxypropionate | — | 7.5 | 7.5 |
| Other ingredients | | | |
| thickener | 0.5 | 0.5 | 0.5 |
| butan-1,3-diol | 13.5 | 13.5 | 13.5 |
| preservative | 0.3 | 0.3 | 0.3 |
| perfume | qs | qs | qs |
| water | to 100 | 100 | 100 |
| pH adjusted with triethanolamine to | 4.0 | 3.8 | 3.8 |

*EMULSENE 1219 is a mixture of cetyl alcohol and polyoxyethylene cetyl ether having an average HLB value of about between 5 and 11.

These emulsions can be prepared by the method described for Examples 1 to 3.

EXAMPLES 7 TO 9

The following formulations illustrate oil-in-water creams according to the invention.

| | % w/w | | |
|---|---|---|---|
| | 7 | 8 | 9 |
| "Oil" | | | |
| mineral oil | 4 | 2 | — |
| paraffin wax | — | 2 | 4 |
| Solid emulsifiers | | | |
| polyoxyethylene(10) cetyl ether | 4 | 4 | 4 |
| cetyl alcohol | 4 | 4 | 4 |
| Amphiphilic compounds | | | |
| 4'-hydroxyerythromycin | 0.1 | — | — |
| hydrocortisone | — | 0.1 | — |
| codeine | — | — | 0.1 |
| Activity enhancer hexan-2,5-diol | 5 | 5 | 5 |
| Other ingredients | | | |
| thickener | 0.3 | 0.3 | 0.3 |
| preservative | 0.4 | 0.4 | 0.4 |
| perfume | qs | qs | qs |
| water | to 100 | 100 | 100 |

EXAMPLES 10 & 11

The following formulations illustrate anti-eczemateous preparations according to the invention.

| | 10 | 11 |
|---|---|---|
| "Oils" | | |
| Ozokerite wax | 5.0 | 10.0 |
| Sirius M85 | 5.0 | 10.0 |
| Solid emulsifier | | |
| Brij 52 | 7.0 | 14.0 |
| Brij 58 | 3.0 | 6.0 |
| Amphiphilic compound erythromycin | 0.25 | 0.5 |
| Activity enhancer polyoxyethylene(2) ethyl ether | 5.0 | 10.0 |
| Other ingredients | | |
| xantham gum | 0.3 | 0.3 |
| perfume | qs | qs |
| preservatives | 0.3 | 0.3 |

EXAMPLES 12 & 13

The following formulations illustrate sun protection products according to the invention.

|  | 12 | 13 |
|---|---|---|
| "Oils" | | |
| carnauba wax | 5.0 | 2.0 |
| linoleic acid | 5.0 | 8.0 |
| Solid emulsifier | | |
| Aldo MSD | 8.0 | 7.0 |
| Brij 58 | 2.0 | 3.0 |
| Amphiphilic compound | 5.0 | 2.5 |
| p-Aminobenzoic acid | | |
| Activity enhancer | 10.0 | 13.5 |
| di(2-hydroxypropyl)ether | | |
| Other ingredients | | |
| xanthan gum | 0.5 | 1.0 |
| preservatives | 0.3 | 0.3 |
| perfume | qs | qs |
| water | to 100 | 100 |

EXAMPLES 14 & 15

The following formulations illustrate anti-pruritic creams according to the invention.

|  | 14 | 15 |
|---|---|---|
| "Oils" | | |
| Beeswax | 5.0 | 10.0 |
| Isopar L | 10.0 | — |
| Solid emulsifier | | |
| Tween 61 | 8.0 | 8.0 |
| Amphiphilic compound | 2.0 | 1.0 |
| Acetyl salicylic acid | | |
| Activity enhancer | 10.0 | 5.0 |
| hexan-2,5-diol | | |
| Other ingredients | | |
| xanthan gum | 0.5 | 1.0 |
| preservatives | 0.3 | 0.3 |
| perfume | qs | qs |
| water | to 100 | 100 |

EXAMPLES 16 & 17

The following formulations illustrate anti-acne products according to the invention:

|  | 16 | 17 |
|---|---|---|
| "Oils" | | |
| Paraffin wax (Mp 55° C.) | 7.0 | 10.0 |
| Sirius M85 | 5.0 | — |
| Solid emulsifiers | | |
| Brij 72 | 1.0 | — |
| Arlacel 165 | 6.0 | 10.0 |
| Amphiphilic compound | 2.0 | 3.2 |
| 2-hydroxyoctanoic acid | | |
| Activity enhancers | | |
| ethyl-2-hydroxypropionate | 7.5 | 5.0 |
| 2-hydroxypropionic acid | 5.0 | 5.0 |
| Other ingredients | | |
| xanthan gum | 0.3 | 0.3 |
| preservatives | 0.3 | 0.3 |
| perfume | qs | qs |
| water | to 100 | 100 | pH adjusted with triethanolamine to pH 4.5

EXAMPLES 18 & 19

The following formulations illustrate local anaesthetic creams according to the invention.

|  | 18 | 19 |
|---|---|---|
| "Oils" | | |
| hexadecane | 10.0 | — |
| silkolene 910 | 1.0 | 20.0 |
| Solid emulsifier | 7.5 | 10.0 |
| Tegester PEG | | |
| Amphiphilic compound | 2.0 | 2.0 |
| codeine | | |
| Activity enhancer | 5.0 | 5.0 |
| pentan-2,4-diol | | |
| Other ingredients | | |
| xanthan gum | 1.0 | 0.5 |
| preservative | 0.3 | 0.3 |
| perfume | qs | qs |
| water | to 100 | 100 |

EXAMPLES 20 & 21

The following formulations illustrate skin lightening compositions according to the invention.

|  | 20 | 21 |
|---|---|---|
| "Oils" | | |
| carnauba wax | 2.0 | 0.5 |
| paraffin wax Mp 55° C. | 2.0 | 7.5 |
| Silkolene 910 | 6.0 | 1.0 |
| oleic acid | 5.0 | 2.5 |
| Solid emulsifiers | | |
| Brij 58 | 3.0 | 3.0 |
| Brij 52 | 7.0 | 7.0 |
| Amphiphilic compound | 2.0 | 3.2 |
| Niacinamide | | |
| Activity enhancer | 10.0 | 13.5 |
| 2-methyl propan-2-ol | | |
| Other ingredients | | |
| xanthan gum | 0.3 | 0.3 |
| preservative | 0.3 | 0.3 |
| perfume | qs | qs |
| water | to 100 | 100 | pH adjusted with triethanolamine to pH 4.5

EXAMPLES 22 & 23

The following formulations illustrate antidandruff hair creams according the invention.

|  | 22 | 23 |
|---|---|---|
| "Oil" | 38.0 | 30.0 |
| Sirius M85 | | |
| Solid emulsifier | 3.0 | 9.0 |
| EMULSENE 1219 | | |
| Amphiphilic compound | 0.5 | 1.0 |
| OCTOPIROX | | |
| Activity enhancer | 7.5 | 13.5 |
| hexan,-2,5-diol | | |
| Other ingredients | | |
| xanthan gum | 1.0 | 1.0 |
| perfume | qs | qs |
| preservatives | 0.3 | 0.3 |

-continued

|  | 22 | 23 |
|---|---|---|
| water | to 100 | 100 |

EXAMPLE 24

The following formulation illustrates a Keratolytic foot lotion according to the invention.

|  | 24 |
|---|---|
| "Oil" | 2.0 |
| Paraffin wax MP 55 | |
| Solid emulsifier | |
| Brij 52 | 2.0 |
| Brij 56 | 1.0 |
| Amphiphilic compound | 5.0 |
| acetyl, salicylic acid | |
| Activity enhancer | 10.0 |
| POE(2) methyl ether | |
| Other ingredients | |
| xanthan gum | 1.0 |
| preservative | 0.3 |
| water | to 100 |

What is claimed is:

1. A cosmetically acceptable product for topical application to human skin which comprises:
   (i) from 0.001 to 20% by weight of an amphiphilic compound selected from the group consisting of 2-hydroxyoctanoic acid, 2-ketooctanoic acid and mixtures thereof;
   (ii) from 1 to 20 by weight of an emulsifier which is normally solid at 20° C., which has an average HLB value of from 5 to 11, and which is capable with water of forming a gel phase having an X-ray reflection of from 0.37 to 0.44 nm and which permits substantially no co-crystallization therewith of the amphiphilic compound;
   (iii) from 0.1 to 50% by weight of an activity enhancer which is capable, at a concentration of 5% by weight of increasing the cloud point temperature of a 0.025M aqueous solution of polyoxyethylene (8) nonylphenyl ether by at least 15° C.; and
   (iv) from 5 to 98.899% by weight of water;
the product having an aqueous phase which forms from 5 to 99% by volume and a gel phase which forms from 1 to 95% by volume.

2. A product according to claim 1, wherein the activity enhancer is capable of increasing the cloud point temperature by at least 20° C.

3. A product according to claim 1, which further comprises up to 75% by weight of oil having a dielectric constant of not greater than 3.0, the product having an oily phase which forms from 2 to 95% by volume.

4. A product according to claim 1 which comprises:
   (i) from 0.001 to 20% by weight of 2-hydroxyoctanoic acid;
   (ii) from 1 to 20% by weight of a mixture of polyoxyethylene(10)cetyl ether and cetyl alcohol;
   (iii) from 0.1 to 50% by weight of butan-1,4-diol;
   (iv) from 1 to 75% by weight of mineral oil; and
   (v) from 9 to 95% by weight of water.

5. A product according to claim 1 which is a gelled, thickened or free flowing liquid.

6. A process for the preparation of a cosmetically acceptable product for topical application to human skin, the product comprising:
   (i) from 0.001 to 20% by weight of an amphiphilic compound having a log partition coefficient in octanol/water of from 0.5 to 3.5; provided that when the amphiphilic compound is one having an unbranched alkyl chain, that chain contains no more than 12 carbon atoms;
   (ii) from 1 to 20% by weight of an emulsifier which is normally solid at 20° C., which has an average HLB value of from 5 to 11, and which is capable with water of forming a gel phase having an X-ray reflection of from 0.37 to 0.44 nm and which permits substantially no cocrystallisation therewith of the amphiphilic compound;
   (iii) from 0.1 to 50% by weight of an activity enhancer which is capable, at a concentration of 5% by weight of increasing the cloud point temperature of a 0.025M aqueous solution of polyoxyethylene(8)nonylphenyl ether by at least 15° C.; and
   (iv) from 5 to 98.899% by weight of water;
the product having an aqueous phase which forms from 5 to 99% by volume and a gel phase which forms from 1 to 95% by volume; the process which comprises the steps of:
   (i) preparing an aqueous phase by mixing with water, watersoluble ingredients, other than the amphiphilic compounds, including activity enhancers, preservatives and humectants, and heating the mixture to a temperature of at least 50° C.;
   (ii) adding to the aqueous phase said emulsifier in melted form with continued heating at a temperature of at least 50° C., and shear mixing to provide an emulsion;
   (iii) cooling the emulsion to form said gel phase;
   (iv) adding with continued stirring the amphiphilic compound; and
   (v) subsequently packaging the product so formed in a sealed container.

7. A process for the preparation of a cosmetically acceptable product for topical application to human skin, the product comprising:
   (i) from 0.001 to 20% by weight of an amphiphilic compound having a log partition coefficient in octanol/water of from 0.5 to 3.5; provided that when the amphiphilic compound is one having an unbranched alkyl chain, that chain contains no more than 12 carbon atoms;
   (ii) from 1 to 20% by weight of an emulsifier which is normally solid at 20° C., which has an average HLB value of from 5 to 11, and which is capable with water of forming a gel phase having an X-ray reflection of from 0.37 to 0.44 nm and which permits substantially no cocrystallisation therewith of the amphiphilic compound;
   (iii) from 0.1 to 50% by weight of an activity enhancer which is capable, at a concentration of 5% by weight of increasing the cloud point temperature of a 0.025M aqueous solution of polyoxyethylene(8)nonylphenyl ether by at least 15° C.;
   (iv) from 1 to 75% by weight of an oil; and
   (v) from 5 to 98.899% by weight of water;
the product having an aqueous phase which forms from 5 to 99% by volume and a gel phase which forms from 1 to 95% by volume; the process which comprises the steps of:
   (i) forming an emulsion between
      (a) an aqueous phase containing water soluble ingredients, other than amphiphilic compounds including activity enhancers, preservatives and humectants;
(b) an oil having a dielectric constant of not greater than 3.0; and
(c) said emulsifier;
at a temperature of at least 50° C.;
(ii) cooling the emulsion to produce said gel phase and to solidify any oil with a melting point above 20° C.;
(iii) adding with stirring the amphiphilic compound; and
(iv) subsequently packaging the emulsion so produced in a sealed container.

* * * * *